(12) United States Patent
Meng

(10) Patent No.: US 8,194,818 B2
(45) Date of Patent: Jun. 5, 2012

(54) CT SCANNER APPARATUS

(75) Inventor: Dazhuang Meng, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 114 days.

(21) Appl. No.: 12/622,275

(22) Filed: Nov. 19, 2009

(65) Prior Publication Data

US 2010/0128842 A1     May 27, 2010

(30) Foreign Application Priority Data

Nov. 21, 2008 (CN) .......................... 2008 1 0176298

(51) Int. Cl.
*H05G 1/64* (2006.01)
*H05G 1/02* (2006.01)
(52) U.S. Cl. .......... 378/19; 378/98.8; 378/193; 378/204
(58) Field of Classification Search ................ 378/4–20, 378/193, 194, 204, 210, 91, 98, 98.8
See application file for complete search history.

(56) References Cited

U.S. PATENT DOCUMENTS

| | | | |
|---|---|---|---|
| 4,912,735 A | 3/1990 | Beer | |
| 5,608,771 A | 3/1997 | Steigerwald et al. | |
| 5,909,100 A | 6/1999 | Watanabe et al. | |
| 7,054,411 B2 | 5/2006 | Katcha et al. | |
| 7,110,488 B2 | 9/2006 | Katcha et al. | |
| 7,197,113 B1 * | 3/2007 | Katcha et al. | 378/101 |
| 2008/0296095 A1 * | 12/2008 | Frank | 187/237 |

* cited by examiner

*Primary Examiner* — Anastasia Midkiff
(74) *Attorney, Agent, or Firm* — Armstrong Teasdale LLP

(57) ABSTRACT

A Computerized Tomography (CT) scanner apparatus includes a scanner gantry, a detector, a detector control panel configured to control the detector, and a power ring. The scanner gantry includes a rotary part and a stationary part, wherein the detector, the detector control panel, and the power ring are mounted in the rotary part. The detector control panel is configured to transmit a scan data signal collected from the detector from the rotary part of the scanner gantry to the stationary part via a power line on the power ring.

18 Claims, 2 Drawing Sheets

CT SCANNER APPARATUS

CROSS REFERENCE TO RELATED APPLICATIONS

This application claims the benefit of Chinese Patent Application No. 200810176298.6 filed Nov. 21, 2008, which is hereby incorporated by reference in its entirety.

BACKGROUND OF THE INVENTION

The embodiments described herein relate to medical device technology, in particular to a Computerized Tomography (CT) scanner apparatus.

The CT scanner apparatus comprises a scanner gantry, an X-ray generator and a detector mounted in the scanner gantry. The scan data collected by the detector, after being processed, must be transmitted from the rotary part of the scanner gantry to the stationary part of the scanner gantry to be further data processed or be displayed on a display. In a CT scanner apparatus, data transmission between the rotary part and the stationary part of the scanner gantry is a technical problem for all CT scanner apparatus to solve. The prior art is to add a slip ring and set a contact point thereon to implement data transmission between the rotary part and the stationary part of the scanner gantry. This type of technical solution can only guarantee reliable data transmission to a certain extent. With the acceleration of rotation speed of the scanner apparatus and the advent of multi-slice scanner device, data generated by the scanner apparatus are also escalating. The existing technical solution cannot meet the demand for higher stability, and is costly at the same time.

BRIEF DESCRIPTION OF THE INVENTION

One aspect provides a CT scanner apparatus, which transmits data over existing power line, thus not only simplifies the transmission path of scan data signal but also reduces cost at the same time.

The CT scanner apparatus comprises a scanner gantry, a detector, a detector control panel for controlling the detector, and a power ring; the scanner gantry comprises a rotary part and a stationary part; the detector, the detector control panel and the power ring are mounted in the rotary part; the detector control panel transmits the scan data signal collected by the detector from the rotary part of the scanner gantry to the stationary part over the power line on the power ring.

Wherein, there are furthermore a first data processor mounted in the rotary part of the scanner gantry and a second data processor mounted in the stationary part of the scanner gantry, the first data processor being connected between the detector control panel and the power ring, transmitting the scan data signal received from the detector control panel to the power line of the power ring; the second data processor being connected via a connection brush to the power line of the power ring, the scan data signal being transmitted from the rotary part of the scanner gantry to the second data processor in the stationary part by the connection brush.

The first data processor and the second data processor are modems having a function of Broadband over Power Line (BPL) signal transmission, which encodes and modulates the scan data signal transmitted from the detector control panel into a signal complying with the power line transfer protocol, receives, decodes and modulates the encoded and modulated scan data signal transmitted from the connection brush on the power ring into signals complying with the internet transport protocol.

The detector control panel and the first data processor are connected to each other by a network cable.

The first data processor is connected by a data line to the power line on the power ring. The joint between the data line and the power line is coupled and fixed by a magnet ring.

Wherein, a computer is further included, which receives the scan data signal transmitted from the second data processor mounted in the stationary part of the scanner gantry, and processes the received scan data signal or displays ton its display.

The second data processor and the computer are connected to each other by a network cable.

The power line couples transmission path of the scan data signal to the transmission path of the power signal, which not only simplifies the signal transmission path, but also omits the slip ring in the prior art, thereby reducing the cost. Besides, with the signal transmission technology of Broadband over Power Line (BPL), the bandwidth may reach 200 Mbps, being able to transmit larger data stream.

DETAILED DESCRIPTION OF THE INVENTION

Following are detailed explanations of the embodiments of the present invention with reference to the figures. The present invention is not limited to these embodiments.

Figure 1:
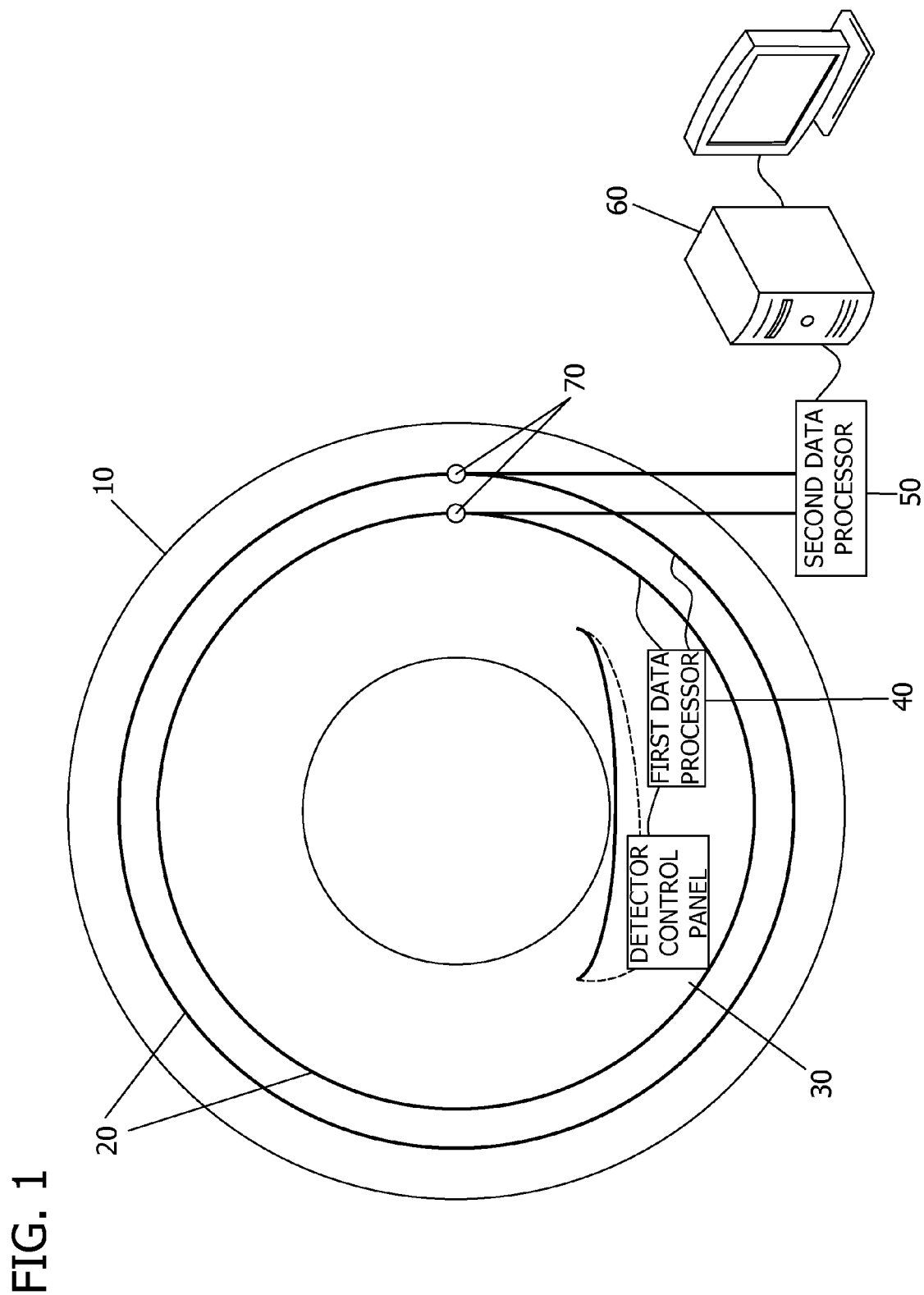
FIG. 1 is a structural representation of the CT scanner apparatus of the present invention.

FIG. 1 is a structural representation of the CT scanner apparatus of the present invention, comprising a scanner gantry 10, a power ring 20, a detector control panel 30 for collecting scan data signal from the detector, a first data processor 40, a second data processor 50 and a controller 60; wherein, the scanner gantry 10 comprises a rotary part and a stationary part, the power ring 20, detector control panel 30 and first data processor 40 are mounted in the rotary part; the second data processor 50 is mounted in the stationary part of the scanner gantry 10. The detector control panel 30 collects the scan data signal and transmits the collected scan data signal by a data line to the first data processor 40. Data is transmitted between the detector control panel 30 and the first data processor 40 with transfer control protocol/internet protocol (TCP/IP), the data line between them being a network cable. By the data line, the first data processor 40 encodes and modulates the received scan data signal into a signal complying with power line transmission and transmits it to the power line of the power ring 20. The second data processor 50 and the power ring 20 are connected via the power ring connection brush 70; by the power ring connection brush 70, the scan data signal encoded and modulated is transmitted to the second data processor 50, which decodes and modulates the received scan data signal into the format complying with TCP/IP protocols and then transmits it to the controller 60. The second data processor 50 and the controller 60 are connected by the data line, the two performing data transmission with TCP/IP protocols, and said data line being a network cable. The controller 60 is a computer, which further processes the received scan data signal or displays it on the display.

Figure 2:
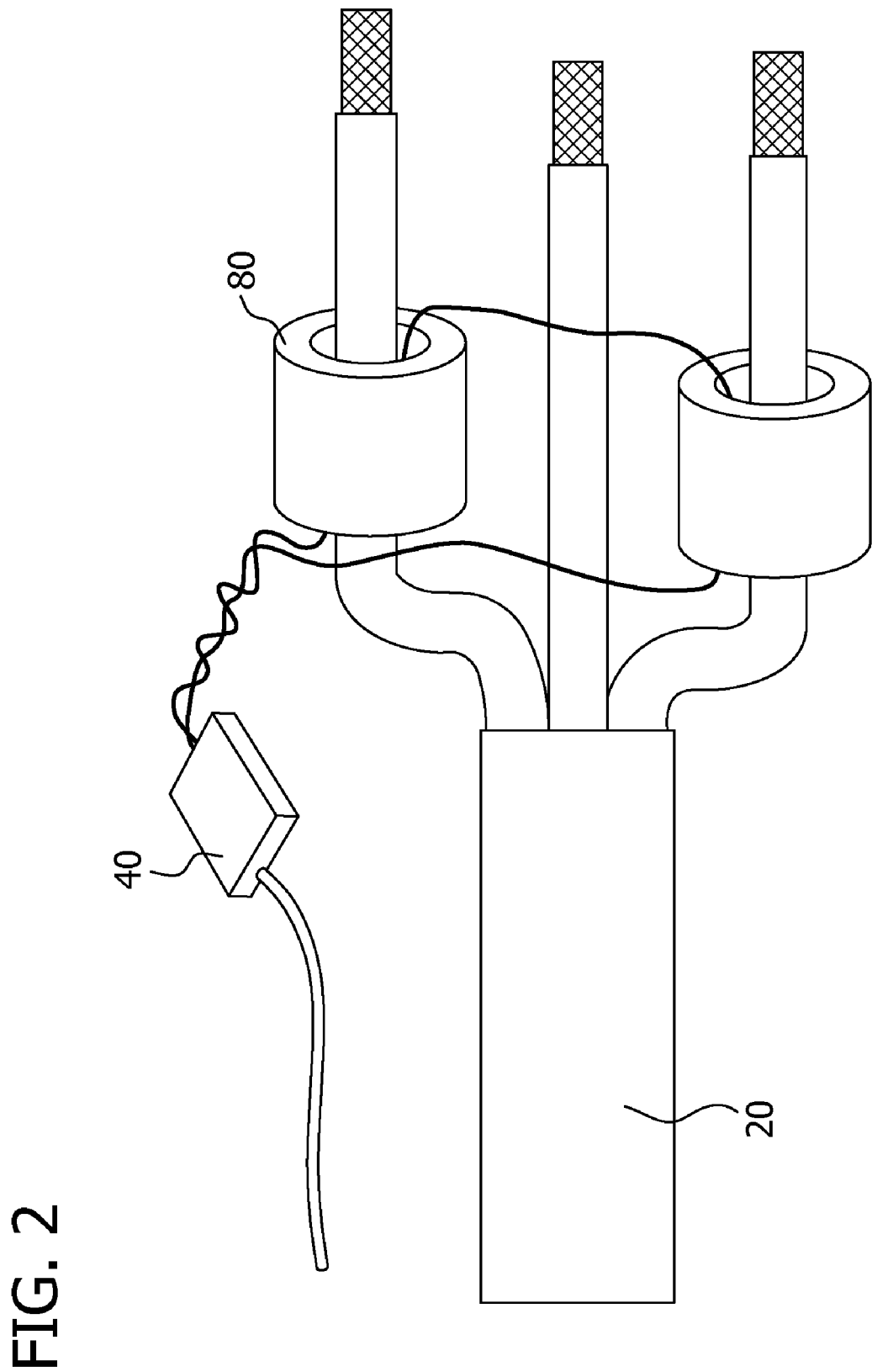
FIG. 2 is a schematic diagram of the coupling of the data processor and the power line in accordance with the present invention.

The power ring 20 comprises a live line and a zero line. FIG. 2 is a schematic diagram showing the connection of the first data processor 40 or the second data processor 50 with the power line on the power ring 20. The first data processor 40 or the second data processor 50 is a modem, which has the signal transmission function of Broadband over Power Line, and is connected with the detector control panel 30 or controller 60 by a data line, such as network cable, is connected to the live line and zero line of the power ring 20 by two data lines. The connection of the data line and the live line or the zero line is coupled and fixed by a magnet ring 80, e.g. ferrite magnet ring. At the same time, the magnet ring 80 also plays the role of filtering the unnecessary noise signal.

In the present invention, the power ring connection brush 70 serves as the dividing line between the rotary part and the stationary part of the scanner gantry 10. From the detector control panel 30 to the power ring connection brush 70, the scan data signal is transferred within the rotary part, but in fact, there is no relative movement between the detector control panel 30 and the power line. From the power ring connection brush 70 to the computer, the scan data signal is transferred within the stationary part. In the present invention, the scan data signal is transmitted from the rotary part of the scanner gantry 10 by the power line of the power ring 20 to the stationary part of the scanner gantry 10, without additionally putting in a slip ring, thus simplifying transmission path and reducing cost.

What is claimed is:

1. A Computerized Tomography (CT) scanner apparatus, comprising:
   a scanner gantry comprising a rotary part and a stationary part;
   a detector;
   a power ring;
   a detector control panel configured to control the detector, wherein the detector, the detector control panel, and the power ring are mounted in the rotary part, and wherein the detector control panel is configured to transmit a scan data signal collected from the detector from the rotary part of the scanner gantry to the stationary part via a power line on the power ring;
   a first data processor mounted in the rotary part of the scanner gantry; and
   a second data processor mounted in the stationary part of the scanner gantry, wherein the first data processor is connected between the detector control panel and the power ring, and is configured to transmit the scan data signal transmitted from the detector control panel to the power line, and wherein the second data processor is connected via a connection brush to the power line of the power ring, and is configured to receive the scan data signal being from the rotary part of the scanner gantry via the connection brush.

2. The CT scanner apparatus according to claim 1, wherein the first data processor and the second data processor each comprises a modem having a function of Broadband over Power Line (BPL) signal transmission, the first data processor and the second data processor each configured to:
   encode and modulate the scan data signal transmitted from the detector control panel into a signal complying with a power line transfer protocol; and
   receive, decode, and modulate the encoded and modulated scan data signal transmitted from the connection brush on the power ring into signals complying with an interne transport protocol.

3. The CT scanner apparatus according to claim 2, wherein the detector control panel and the first data processor are connected to each other by a network cable.

4. The CT scanner apparatus according to claim 3, wherein the first data processor is connected by a data line to the power line on the power ring, such that a joint between the data line and the power line is coupled and fixed by a magnet ring.

5. The CT scanner apparatus according to claim 1, further comprising a computer configured to:
   receive the scan data signal transmitted from the second data processor mounted in the stationary part of the scanner gantry; and
   one of process the received scan data signal and display the received scan data signal using a display.

6. The CT scanner apparatus according to claim 5, wherein the second data processor and the computer are connected to each other by a network cable.

7. The CT scanner apparatus according to claim 2, further comprising a computer configured to:
   receive the scan data signal transmitted from the second data processor mounted in the stationary part of the scanner gantry; and
   one of process the received scan data signal and display the received scan data signal using a display.

8. The CT scanner apparatus according to claim 7, wherein the second data processor and the computer are connected to each other by a network cable.

9. The CT scanner apparatus according to claim 3, further comprising a computer configured to:
   receive the scan data signal transmitted from the second data processor mounted in the stationary part of the scanner gantry; and
   one of process the received scan data signal and display the received scan data signal using a display.

10. The CT scanner apparatus according to claim 9, wherein the second data processor and the computer are connected to each other by a network cable.

11. The CT scanner apparatus according to claim 4, further comprising a computer configured to:
    receive the scan data signal transmitted from the second data processor mounted in the stationary part of the scanner gantry; and
    one of process the received scan data signal and display the received scan data signal using a display.

12. The CT scanner apparatus according to claim 11, wherein the second data processor and the computer are connected to each other by a network cable.

13. A method of assembling a Computerized Tomography (CT) scanner apparatus, comprising:
    providing a scanner gantry that includes a rotary part and a stationary part;
    mounting a detector, a detector control panel, and a power ring in the rotary part of the scanner gantry;
    connecting the detector control panel to a power line on a power ring to facilitate transmitting a scan data signal by the detector control panel from the rotary part to the stationary part;
    mounting a first data processor in the rotary part of the scanner gantry; and
    connecting the first data processor to the detector control panel and connecting the first data processor to the power ring, wherein the first data processor is configured to transmit the scan data signal from the detector control panel to the power line of the power ring.

14. The method according to claim 13, wherein connecting the first data processor to the detector control panel comprises connecting the first data processor to the detector control panel via a network cable.

15. The method according to claim 13, wherein connecting the first data processor to the power ring comprises connecting the first data processor to the power line via a data line such that a joint between the data line and the power line is coupled and fixed by a magnet ring.

16. The method according to claim 13, further comprising:
mounting a second data processor in the stationary part of the scanner gantry; and
connecting the second data processor to a connection brush, wherein the second data processor is configured to receive the scan data signal being from the rotary part of the scanner gantry via the connection brush.

17. The method according to claim 16, further comprising connecting a computer to the second processor via a network cable, wherein the computer is configured to receive the scan data signal from the second data processor and to one of process the scan data signal and display the scan data signal using a display.

18. A Computerized Tomography (CT) scanner apparatus, comprising:
a scanner gantry comprising a rotary part and a stationary part;
a detector;
a detector control panel configured to control the detector;
a power ring comprising a power line;
a computer connected to the power line via a connection brush, wherein the detector, the detector control panel, and the power ring are mounted in the rotary part, and wherein the detector control panel is configured to transmit a scan data signal collected from the detector to the computer via the power line on the power ring;
a first data processor mounted in the rotary part of the scanner gantry; and
a second data processor mounted in the stationary part of the scanner gantry, wherein the first data processor is connected between the detector control panel and the power ring, and is configured to transmit the scan data signal transmitted from the detector control panel to the power line, and wherein the second data processor is connected via a connection brush to the power line of the power ring, and is configured to receive the scan data signal being from the rotary part of the scanner gantry via the connection brush.

* * * * *